(12) United States Patent
Ziche et al.

(10) Patent No.: US 10,392,479 B2
(45) Date of Patent: Aug. 27, 2019

(54) PLATINUM COMPLEXES AND THEIR USE IN COMPOUNDS THAT CAN BE CROSS-LINKED BY A HYDROSILYLATION REACTION

(71) Applicant: Wacker Chemie AG, Munich (DE)

(72) Inventors: Wolfgang Ziche, Burghausen (DE); Andreas Koellnberger, Kirchdorf (DE)

(73) Assignee: WACKER CHEMIE AG, Munich (DE)

( * ) Notice: Subject to any disclaimer, the term of this patent is extended or adjusted under 35 U.S.C. 154(b) by 231 days.

(21) Appl. No.: 15/505,632

(22) PCT Filed: Aug. 24, 2015

(86) PCT No.: PCT/EP2015/069345
§ 371 (c)(1),
(2) Date: Feb. 22, 2017

(87) PCT Pub. No.: WO2016/030325
PCT Pub. Date: Mar. 3, 2016

(65) Prior Publication Data
US 2017/0349717 A1  Dec. 7, 2017

(30) Foreign Application Priority Data
Aug. 26, 2014 (DE) ........................ 10 2014 217 003

(51) Int. Cl.
| | |
|---|---|
| *C08G 77/08* | (2006.01) |
| *C08J 3/24* | (2006.01) |
| *C07F 15/00* | (2006.01) |
| *C08L 83/04* | (2006.01) |
| *C07F 17/02* | (2006.01) |
| *C08G 77/38* | (2006.01) |
| *C08K 5/56* | (2006.01) |
| *C08L 83/00* | (2006.01) |
| *B01J 31/16* | (2006.01) |
| *C08G 77/20* | (2006.01) |
| *C08G 77/12* | (2006.01) |

(52) U.S. Cl.
CPC ............ *C08J 3/24* (2013.01); *C07F 15/0086* (2013.01); *C07F 17/02* (2013.01); *C08G 77/38* (2013.01); *C08K 5/56* (2013.01); *C08L 83/00* (2013.01); *C08L 83/04* (2013.01); *B01J 31/1608* (2013.01); *C08G 77/12* (2013.01); *C08G 77/20* (2013.01); *C08J 2383/07* (2013.01); *C08L 2312/06* (2013.01)

(58) Field of Classification Search
CPC .............................. C08G 77/08; B01J 31/1608
USPC ........................................................... 528/15
See application file for complete search history.

(56) References Cited

U.S. PATENT DOCUMENTS

| | | | | |
|---|---|---|---|---|
| 4,510,094 A | * | 4/1985 | Drahnak | C07F 15/0086 522/66 |
| 4,600,484 A | * | 7/1986 | Drahnak | C07F 15/0086 204/157.74 |
| 4,916,169 A | * | 4/1990 | Boardman | A61K 6/10 522/104 |
| 6,127,446 A | * | 10/2000 | Butts | C07F 15/0086 522/29 |
| 8,088,878 B2 | * | 1/2012 | Koellnberger | C07F 17/02 502/152 |
| 2010/0292361 A1 | * | 11/2010 | Koellnberger | C07F 17/02 522/172 |

FOREIGN PATENT DOCUMENTS

| | | |
|---|---|---|
| EP | 0146307 B1 | 6/1985 |
| EP | 1803728 A1 | 7/2007 |
| EP | 2238145 B1 | 10/2010 |
| JP | 2010248446 A2 | 11/2010 |
| WO | 2009092762 A1 | 7/2009 |

OTHER PUBLICATIONS

Xue, Ziling et al., "Characterization of (Methylcyclopentadienyl)trimethylplatinum and Low-Temperature Organometallic Chemical Vapor Deposition of Platinum Metal", J. Am. Chem. Soc. 1989, 111, 8779-8784.
Galakhov, Mikhail V. et al., "Intramolecular coordination of an alkene to a mixed dicyclopentadienyl benzyl zirconium cation studied by NMR spectroscopy" Chem. Commun., 1998, pp. 17-18.
Boardman, Larry et al., "195Pt NMR Study of (n5-cyclopentadienyl)trialkylplatinum(IV) Complexes", Magnetic Resonance in Chemistry, vol. 30, 481-489 (1992).

* cited by examiner

*Primary Examiner* — Margaret G Moore
(74) *Attorney, Agent, or Firm* — Brooks Kushman P.C.

(57) ABSTRACT

Cyclopentadienyl platinum complexes bearing ethylenic unsaturation are efficient photocatalysts for hydrosilylation of compounds containing aliphatic carbon-carbon multiple bonds, while exhibiting extended dark time, and are particularly useful in addition-curable organopolysiloxane compositions.

13 Claims, No Drawings

PLATINUM COMPLEXES AND THEIR USE IN COMPOUNDS THAT CAN BE CROSS-LINKED BY A HYDROSILYLATION REACTION

CROSS REFERENCE TO RELATED APPLICATIONS

This application is the U.S. National Phase of PCT Appln. No. PCT/EP2015/069345 filed Aug. 24, 2015, which claims priority to German Application No. 10 2014 217 003.6 filed Aug. 26, 2014, the disclosures of which are incorporated in their entirety by reference herein.

BACKGROUND OF THE INVENTION

1. Field of the Invention

The present invention relates to platinum complexes, especially to platinum catalysts activatable by ultraviolet and/or visible radiation, to the preparation thereof, to the use thereof in crosslinkable compositions, and to crosslinking products produced therefrom, such as silicone elastomers produced by irradiation.

2. Description of the Related Art

In general, in addition-crosslinking silicone compositions, the crosslinking operation is effected via a hydrosilylation reaction in which the catalyst used is typically platinum or another metal from the platinum group. In the reaction that proceeds catalytically, aliphatically unsaturated groups are reacted with Si-bonded hydrogen, in order to convert the addition-crosslinkable silicone composition to the elastomeric state via the formation of a network.

According to the prior art, the activation of the catalysts used is normally effected by thermal means, meaning that the addition-crosslinkable silicone composition consequently has to be heated for the crosslinking operation. In this case, the silicone composition frequently has to be applied to a substrate, as is the case, for example, in coating operations and in selected potting, molding and coextrusion or other shaping methods. The actual vulcanization operation in this case is effected by a heating process, for which costly and energy-intensive equipment often has to be operated.

The use of mixtures crosslinkable by means of ultraviolet and/or visible radiation is accordingly accompanied in many applications by a cost saving which is considerable in some cases. As a result, it is possible to achieve a saving of energy and process costs and hence a corresponding rise in productivity. In addition, crosslinking by means of ultraviolet and/or visible radiation often enables continuous manufacture which brings further productivity advantages compared to a discontinuous batchwise process. A further advantage arises from the fact that, especially in the case of multipart components, for example hard-soft composites which contain a thermoplastic, for example, as a composite partner alongside an elastomeric material, dispensing with a high-temperature manufacturing step prevents thermal warpage of the component.

The technical literature describes a multitude of platinum complexes suitable for initiation of a hydrosilylation reaction by means of radiation. All the platinum catalysts described can be activated by light and, even after the light source has been switched off, are capable of crosslinking silicone compositions. This operation is known to those skilled in the art, as a "dark reaction."

Dark stability, by contrast, describes the stability of a composition containing photo activatable catalysts in the dark, i.e. ultimately the technically desirable storage stability of a composition.

EP 0 146 307 B1 discloses ($\eta^5$-cyclopentadienyl)tri($\sigma$-alkyl)-platinum(IV) complexes which feature good solubility in the silicone matrix.

EP 1 803 728 A1 discloses modified ($\eta^5$-cyclopentadienyl)tri($\sigma$-alkyl)platinum(IV) complexes bearing specific substituents (naphthyl, anthracenyl, etc.) on the cyclopentadienyl ring, in order to increase the quantum yield and in order to shift the light wavelength required for activation into the long-wave range. However, the attachment of aromatic rings has an adverse effect on the solubility of the complexes in the silicone matrix. All the ($\eta^5$-cyclopentadienyl)tri($\sigma$-alkyl)platinum(IV) complexes disclosed bear exclusively radicals on the cyclopentadienyl ligand that do not disrupt any hydrosilylation reaction, i.e. in particular, no unsaturated radicals.

EP 2 238 145 B1 describes the attachment of ($\eta^5$-cyclopentadienyl)tri($\sigma$-alkyl)platinum(IV) complexes to polymers, in order to reduce the volatility of this compound class. No unsaturated radicals in the complex are listed by way of example. The theoretical option of attachment via unsaturated radicals is discussed. The unsaturated radicals on the complex that are claimed in general terms do not include any silyl radicals.

A common factor in all the compositions claimed in the prior art that contain ($\eta^5$-cyclopentadienyl)tri($\sigma$-alkyl)platinum(IV) complexes is that there is no description of any modification for increasing the dark stability.

Royo describes, for metallocenes of the early transition metals, allylsilyl-substituted cyclopentadienyl radicals (Chem. Commun. 1998, 17). The allylsilyl radical is particularly suitable for stabilization of cationic metal centers that arise through the loss of $\sigma$-bonded alkyl radicals. No metallocenes of this kind are described for late transition metals such as platinum.

In summary, it can be stated that none of the silicone compositions crosslinkable via visible and/or UV radiation that are known to date satisfactorily meet the demands placed on such silicone compositions that can be employed especially for production in the industrial sector.

SUMMARY OF THE INVENTION

It was therefore an object of the present invention to provide suitable platinum catalysts. It was a further object of the present invention to provide silicone compositions that do not have the abovementioned disadvantages, especially the inadequate dark stability. These and other objects are surprisingly and unexpectedly achieved by providing platinum complexes of the general formula $$R^3{}_3Pt\{CpR^4{}_{5-r-t}[(CR_2)_nSiR^1{}_oR^2{}_p]_t[SiR^7{}_sR^8{}_{3-s}]_r\} \qquad (I)$$

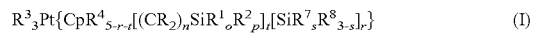

where
Cp is a cyclopentadienyl radical,
n is an integer from 1 to 8,
o is 0, 1, 2 or 3,
p is 0, 1, 2 or 3, with the proviso that o+p=3,
r is 1, 2, 3, 4 or 5, preferably 1, 2 or 3, more preferably 1 or 2, especially 1,
t is 0, 1, 2, 3 or 4, preferably 0 or 1, more preferably 1, with the proviso that r+t≤5, preferably 3,
s is 0, 1 or 2, preferably 2, R may be the same or different and is a hydrogen atom or a monovalent unsubstituted or substituted hydrocarbyl radical, $R^1$ may be the same or different and is a monovalent unsubstituted or substituted hydrocarbyl radical which may be interrupted by heteroatoms, $R^2$ may be the same or different and is a hydrolyzable group or an oxygen-bonded siloxy radical, $R^7$ may be the same or different and is a monovalent, unsubstituted or substituted, aliphatically saturated hydrocarbyl radical which may be interrupted by heteroatoms, or an oxygen-bonded siloxy radical, $R^8$ may be the same or different and is an aliphatically unsaturated, optionally substituted radical, $R^3$ may be the same or different and is a monovalent, unsubstituted or substituted, aliphatically saturated hydrocarbyl radical, $R^4$ may be the same or different and is a hydrogen atom, SiC-bonded silyl radical or an unsubstituted or substituted hydrocarbyl radical which may be interrupted by heteroatoms.

DETAILED DESCRIPTION OF THE PREFERRED EMBODIMENTS

Cyclopentadienyl radical Cp is known from the literature. Preferably, cyclopentadienyl radical Cp understood in the context of the present invention to mean the cyclopentadienyl anion, which consists of a singly negatively charged, aromatic five-membered ring system $C_5R'_5{}^-$. Cyclopentadienylplatinum complexes in the context of the invention contain a cyclopentadienyl radical $\eta^5$-bonded to a platinum-containing fragment M

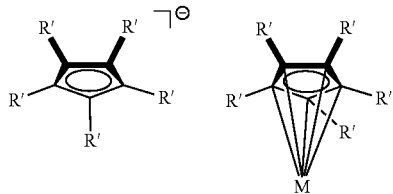

where R' represents any desired radicals, which may also be joined to one another to form fused rings.

Examples of $R^1$ radicals are alkyl radicals such as the methyl, ethyl, n-propyl, isopropyl, n-butyl, sec-butyl, isobutyl, tert-butyl, n-pentyl, sec-pentyl, isopentyl, neopentyl, and tert-pentyl radicals; hexyl radicals, such as the n-hexyl radical; heptyl radicals such as the n-heptyl radical; octyl radicals such as the n-octyl radical and isooctyl radicals such as the 2,4,4-trimethylpentyl radical; nonyl radicals such as the n-nonyl radical; decyl radicals such as the n-decyl radical; dodecyl radicals such as the n-dodecyl radical; hexadecyl radicals such as the n-hexadecyl radical; octadecyl radicals such as the n-octadecyl radical; cycloalkyl radicals, such as the cyclopentyl, cyclohexyl, cycloheptyl and methyl-cyclohexyl radicals; alkenyl radicals such as the vinyl, 1-propenyl, 2-propenyl, n-5-hexenyl, 4-vinylcyclohexyl and 3-norbornenyl radicals; aryl radicals such as the phenyl, naphthyl, anthryl and phenanthryl radicals; alkaryl radicals such as the o-, m- and p-tolyl, xylyl, mesitylenyl and o-, m- and p-ethylphenyl radical; and aralkyl radicals, such as the benzyl radical and the α- and β-phenylethyl radicals.

Examples of substituted $R^1$ radicals are haloalkyl radicals such as the 3,3,3-trifluoro-n-propyl radical, the 2,2,2,2',2', 2'-hexafluoroisopropyl radical and the heptafluoroisopropyl radical, and haloaryl radicals, such as the o-, m- and p-chlorophenyl radical.

Preferably, the $R^1$ radical comprises monovalent hydrocarbyl radicals having 1 to 30 carbon atoms, which may be interrupted by heteroatoms such as O, N, S or P, more preferably monovalent, aliphatically saturated hydrocarbyl radicals having 1 to 8 carbon atoms, especially the methyl or phenyl radical, and most preferably the methyl radical.

Examples of R radicals are a hydrogen atom and the examples cited for the $R^1$ radical.

Preferably, the R radical comprises a hydrogen atom or hydrocarbyl radicals having 1 to 30 carbon atoms, more preferably hydrogen or linear saturated hydrocarbyl radicals having 1 to 8 carbon atoms, especially a hydrogen atom.

Preferably, the hydrolyzable $R^2$ radicals are carboxyl radicals —O—C(O)$R^5$, oxime radicals —O—N=$CR^5{}_2$, organyloxy radicals —$OR^5$, amide radicals —$NR^6$—C(O)$R^5$, amine radicals —$NR^6{}_2$ or aminooxy radicals —O—$NR^6{}_2$, where $R^5$ and $R^6$ may each be the same or different and are as defined for R, more preferably carboxyl radicals or organyloxy radicals.

Preferably, the $R^5$ radical comprises hydrocarbyl radicals having 1 to 6 carbon atoms, which may be interrupted by oxygen atoms, more preferably hydrocarbyl radicals having 1 to 3 carbon atoms.

Preferably, the $R^6$ radical comprises hydrocarbyl radicals having 1 to 6 carbon atoms, more preferably hydrocarbyl radicals having 1 to 3 carbon atoms.

Examples of siloxy radicals $R^2$ are linear or branched oligo- and polysiloxy radicals having 1 to 5000 siloxy units containing dimethylsiloxy, phenylmethylsiloxy, diphenylsiloxy, methylsiloxy, phenylsiloxy or $SiO_{4/2}$ units, and bearing hydroxyl, trimethylsilyl, dimethylsilyl or vinyl end groups.

Preferably, $R^2$ as a siloxy radical comprises those of the formula $$-(OSiR^9{}_2)_m-R^9 \qquad (II)$$

where m is an integer from 1 to 5000, preferably 8 to 50, and $R^9$ may be the same or different and is as defined for the $R^1$ radical.

Preferably, the $R^2$ radical comprises alkoxy, carboxyl or siloxy radicals, more preferably methoxy, acetoxy, 2-methoxyethoxy groups or siloxy radicals —(OSiMe$_2$)$_{8-500}$-CH=CH$_2$ or —(OSiMe$_2$)$_{8-500}$-CH$_3$ with Me being the methyl radical.

Examples of the $R^7$ radical are the examples cited for the $R^1$ radical, of optionally substituted, aliphatically saturated hydrocarbyl radicals, and the examples cited for the $R^2$ radical, of siloxy radicals.

Preferably, the $R^7$ radical comprises monovalent, aliphatically saturated hydrocarbyl radicals which have 1 to 30 carbon atoms, may be substituted by halogen atoms and may be interrupted by heteroatoms such as O, N, S or P, more preferably monovalent, aliphatically saturated hydrocarbyl radicals having 1 to 8 carbon atoms, especially the methyl or phenyl radical, most preferably the methyl radical.

Examples of $R^8$ radicals are the examples cited for the $R^1$ radical, of optionally substituted, aliphatically unsaturated hydrocarbyl radicals.

Preferably, the $R^8$ radical comprises radicals of the formula —$CR^{10}{}_2$—$CR^{10}$=$CR^{10}{}_2$ where $R^{10}$ may be the same or different and is as defined for the R radical.

Preferably, the $R^{10}$ radical comprises hydrogen or a hydrocarbyl radical having 1 to 30 carbon atoms, more preferably hydrogen or a linear saturated hydrocarbyl radical having 1 to 8 carbon atoms, especially a methyl radical or hydrogen, most preferably hydrogen.

Examples of the $R^3$ radical are the examples cited for the $R^1$ radical, of optionally substituted hydrocarbyl radicals.

Preferred $R^3$ radicals are aliphatic hydrocarbyl radicals which have 1 to 30 carbon atoms, are optionally substituted by halogen, silyl or aryl radicals, and may be interrupted by heteroatoms such as O, N, S or P, more preferably linear or branched alkyl radicals having 1 to 12 carbon atoms, especially the methyl radical.

The $R^4$ radical as an optionally substituted hydrocarbyl radical which may be interrupted by heteroatoms is mono- or polyvalent, preferably monovalent. Two or more monovalent $R^4$ radicals may also form one or more rings which are fused to the cyclopentadienyl radical and may be aromatic, saturated or aliphatically unsaturated. It is also possible for a polyvalent $R^4$ radical to be bonded to the cyclopentadienyl radical via more than one point and to form one or more rings which are fused to the cyclopentadienyl radical and may be aromatic, saturated or aliphatically unsaturated.

Examples of the $R^4$ radical are the examples cited for the R radical, of monovalent, optionally substituted hydrocarbyl radicals and SiC-bonded silyl radicals $SiR^7_3$, for example trialkylsilyl radicals. Examples of fused rings formed by joined monovalent or divalent $R^4$ radicals are benzo, naphtho, cyclopenta or cyclohexa groups.

Preferably, the $R^4$ radical comprises hydrogen or monovalent hydrocarbyl radicals which have 1 to 30 carbon atoms, are optionally substituted by halogen atoms and may be interrupted by heteroatoms such as O, N, S or P, or benzo radicals or trialkylsilyl radicals, more preferably hydrogen or monovalent, aliphatically saturated hydrocarbyl radicals having 1 or 8 carbon atoms or benzo radicals, especially hydrogen or the methyl radical.

Examples of inventive platinum complexes of the formula (I) are
trimethyl[(allyldimethylsilyl)cyclopentadienyl]platinum (IV),
trimethyl[((2-methylallyl)dimethylsilyl)cyclopentadienyl]platinum(IV),
trimethyl[(trimethoxysilyl)methyl(allyldimethylsilyl)cyclopentadienyl]platinum(IV),
trimethyl[(2-trimethoxysilyl)ethyl(allyldimethylsilyl)cyclopentadienyl]platinum(IV),
trimethyl[(3-trimethoxysilyl)propyl(allyldimethylsilyl) cyclopentadienyl]platinum(IV),
trimethyl[(3-dimethoxymethylsilyl)propyl(allyldimethylsilyl)cyclopentadienyl]platinum(IV),
trimethyl[(4-trimethoxysilyl)butyl(allyldimethylsilyl)cyclopentadienyl]platinum(IV),
trimethyl[(2-trimethoxysilyl)-1-methylethyl-(allyldimethylsilyl)cyclopentadienyl]platinum(IV),
trimethyl[(3-trimethoxysilyl)-2-methyl-2-propyl-(allyldimethylsilyl)cyclopentadienyl]platinum(IV),
trimethyl[bis(allyldimethylsilyl)cyclopentadienyl]platinum(IV),
trimethyl[bis(2-methylallyldimethylsilyl)cyclopentadienyl]platinum(IV),
trimethyl[(trimethoxysilyl)methylbis(allyldimethylsilyl) cyclopentadienyl]platinum(IV),
trimethyl[(2-trimethoxysilyl)ethylbis(allyldimethylsilyl) cyclopentadienyl]platinum(IV),
trimethyl[(3-trimethoxysilyl)propylbis(allyldimethylsilyl)cyclopentadienyl]platinum(IV),
trimethyl[(4-trimethoxysilyl)butylbis(allyldimethylsilyl) cyclopentadienyl]platinum(IV),
trimethyl[(2-trimethoxysilyl)-1-methylethylbis(allyldimethylsilyl)cyclopentadienyl]platinum(IV),
trimethyl[(3-trimethoxysilyl)-2-methyl-2-propylbis(allyldimethylsilyl)cyclopentadienyl]platinum(IV),
trimethyl[tris(allyldimethylsilyl)cyclopentadienyl]platinum(IV),
trimethyl[(triethoxysilyl)methyl(allyldimethylsilyl)cyclopentadienyl]platinum(IV),
trimethyl[(triacetoxysilyl)methyl(allyldimethylsilyl)cyclopentadienyl]platinum(IV),
trimethyl[(3-bistrimethylsiloxy)methylsilylpropyl](allyldimethylsilyl)cyclopentadienylplatinum(IV),
trimethyl[(3-triethoxysilyl)propyl(allyldimethylsilyl)cyclopentadienyl]platinum(IV),
trimethyl[(triethoxysilyl)methylbis(allyldimethylsilyl)cyclopentadienyl]platinum(IV),
trimethyl[(3-triethoxysilyl)propylbis(allyldimethylsilyl) cyclopentadienyl]platinum(IV),
trimethyl[(triethoxysilyl)methyltris(allyldimethylsilyl) cyclopentadienyl]platinum(IV),
triethyl[(allyldimethylsilyl)cyclopentadienyl]platinum (IV),
tris(trimethylsilylmethyl)[(allyldimethylsilyl)cyclopentadienyl]platinum(IV),
triethyl[(trimethoxysilyl)methyl(allyldimethylsilyl)cyclopentadienyl]platinum(IV),
triethyl[(trimethoxysilyl)methylbis(allyldimethylsilyl)cyclopentadienyl]platinum(IV),
triethyl[tris(allyldimethylsilyl)cyclopentadienyl]platinum (IV) and
triethyl[(trimethoxysilyl)methyltris(allyldimethylsilyl) cyclopentadienyl]platinum(IV).

Preferably, the platinum complexes of the invention are
trimethyl[(allyldimethylsilyl)cyclopentadienyl]platinum (IV),
trimethyl[bis(allyldimethylsilyl)cyclopentadienyl]platinum(IV),
trimethyl[(3-dimethoxymethylsilyl)propyl(allyldimethylsilyl)cyclopentadienyl]platinum(IV),
trimethyl[(3-trimethoxysilyl)propylbis(allyldimethylsilyl)cyclopentadienyl]platinum(IV) and
trimethyl[(3-trimethoxysilyl)propyl(allyldimethylsilyl) cyclopentadienyl]platinum(IV),
more preferably
trimethyl[(allyldimethylsilyl)cyclopentadienyl]platinum (IV),
trimethyl[(3-dimethoxymethylsilyl)propyl(allyldimethylsilyl)cyclopentadienyl]platinum(IV) and
trimethyl[(3-trimethoxysilyl)propyl(allyldimethylsilyl) cyclopentadienyl]platinum(IV),
especially
trimethyl[(allyldimethylsilyl)cyclopentadienyl]platinum (IV) and
trimethyl[(3-dimethoxymethylsilyl)propyl(allyldimethylsilyl)cyclopentadienyl]platinum(IV).

The inventive platinum complexes of the formula (I) are air-stable and, in the absence of hydrolyzable radicals, moisture-stable compounds. They are labile with respect to irradiation, and so they can be photochemically activated and catalyze hydrosilylation reactions.

Platinum complexes of the formula (I) that have been provided with hydrolyzable $R^2$ radicals can be converted to polymer-bound complexes by known methods of siloxane chemistry, such as (co)hydrolysis, (co)condensation or equilibration, such that $R^2$ is a siloxy radical.

The inventive platinum complexes of the formula (I) have the advantage that they are easily preparable and are air-stable and, in the absence of hydrolyzable radicals, moisture-stable. They are activatable with standard radiation sources and in that case act as hydrosilylation catalysts. Apart from exclusion of light, preferably no additional measures are needed in the handling of the complexes and the formulation of preparations containing the complexes.

The inventive platinum complexes of the general formula (I) are preferably prepared by reacting a platinum precursor with a silylcyclopentadienide salt containing at least one aliphatically unsaturated hydrocarbyl radical on the silicon atom in an aprotic solvent, for example diethyl ether, tetrahydrofuran, furan, ethyl acetate and methyl acetate, at temperatures of −78 to 100° C. and a pressure of the surrounding atmosphere, i.e. about 1013 hPa, and under inert gas. If necessary, salts formed are dissolved with water and the organic phase is devolatilized under reduced pressure, the platinum complexes, if they are suitable in terms of volatility, are distilled under reduced pressure and at temperatures up to 100° C. The purification of the complex is also possible by crystallization, sublimation, chromatography, extraction or other standard methods. The synthesis and purification methods are based on methods known to those skilled in the art.

All the synthesis steps are preferably effected with exclusion of short-wave light having a wavelength of less than 500 nm. Conditions of this kind are known to those skilled in the art, for example, from photolithography, where photochemically inactive illumination ("yellow light") is used.

Platinum precursor used in accordance with the invention preferably comprises commercially available trialkyl-platinum(IV) halides, for example $(Me_3PtI)_4$, $(Me_3PtCl)_4$ or $(Me_3PtCl)_4$ with Me being the methyl radical. Preferably, the silylcyclo-pentadienide, prior to the reaction with the platinum precursor, is prepared by deprotonation from the corresponding silylcyclopentadiene and a strong base, for example LiH, NaH, KH, n-butyllithium or t-butyllithium. The synthesis can be effected by standard chemical methods. Reference is made here, for example, to Magnetic Resonance in Chemistry 1992, 30, 481 or J. Am. Chem. Soc. 1989, 111, 8779.

The inventive platinum complexes of the general formula (I) with t>0 and $R^2$ as a hydrolyzable radical additionally have the advantage that, after the appropriate purification of the complexes, they can be (co)hydrolyzed and condensed into a siloxane matrix and hence are in polymer-bound form. The inventive preparation of the complexes of the formula (I) in high purity by standard techniques and the subsequent optional attachment to the siloxane matrix reduces both the vapor pressure and the bioavailability of the catalyst from the silicone matrix, both in uncrosslinked and in crosslinked silicone mixtures.

(Co)hydrolysis and (co)condensation with other organosilicon compounds likewise bearing hydrolyzable or condensable groups is a process step known to those skilled in the art. Examples of suitable organosilicon compounds which can be used in the process of the invention are alkoxysilanes such as dimethyldimethoxysilane, methyltrimethoxysilane, vinyltrimethoxysilanes, dodecylmethyldiethoxysilane, n-octadecyltrimethoxysilane, hexamethoxydisilane, 1,1,3,3-tetraethoxy-1,3-dimethyldisiloxane, 3-chloropropyltriethoxysilane, and siloxanes such as vinyltris(dimethylsiloxy)silanes, 1,1,3,3-tetramethyl-1,3-diethoxydisiloxane, α,ω-silanol-terminated polydimethylsiloxanes [CAS 70131-67-8], α,ω-silanol-terminated diphenylsiloxane-dimethylsiloxane copolymers [CAS 68951-93-9, 68083-14-7], α,ω-silanol-terminated polydiphenylsiloxanes [CAS 63148-59-4], α,ω-silanol-terminated polytrifluoropropylmethylsiloxanes [CAS 68607-77-2] and silanol-trimethylsilyl-modified Q resins [CAS 56275-01-5].

For the cohydrolysis optionally conducted in accordance with the invention, it is possible to use catalysts known to those skilled in the art, for example acids, alkalis or Zn compounds, Al compounds or Sn compounds, for example bis(2,4-pentanedionate)zinc, aluminum tris(2,4-pentanedionate), trifluoroacetic acid or acetic acid.

The present invention further provides a process for preparing the inventive platinum complexes of the formula (I), characterized in that cyclopentadienide salts are reacted with triorganoplatinum(IV) halides.

The process of the invention has the advantage that the organic chemistry syntheses known to those skilled in the art can be used to prepare a multitude of substituted cyclopentadienes which can then be converted by known metalation methods in a simple manner to the corresponding cyclopentadienides. It is an advantage of the process that it is possible to react the cyclopentadienides with triorganoplatinum(IV) halides of good commercial availability, and that the exclusion of light is only needed from this process step onward.

The process of the invention also has the advantage that platinum complexes of the formula (I) can be prepared in high purity, and on this basis the preparation of one-component, addition-crosslinkable mixtures is possible.

The platinum complexes of the invention, or those prepared in accordance with the invention, can be used for all purposes for which platinum complexes have been used to date.

The platinum catalysts of the invention are useful as catalysts for hydrosilylation reactions, in which the activation is effected by means of ultraviolet or visible radiation.

The invention further provides addition-crosslinking compositions, characterized in that they comprise platinum complexes of the formula (I).

Preferably, the compositions of the invention are those comprising
(i) at least one compound selected from the group comprising compounds (A), (B) and (C), where
(A) is an organic compound and/or an organosilicon compound containing at least two radicals having aliphatic carbon-carbon multiple bonds,
(B) is an organosilicon compound containing at least two Si-bonded hydrogen atoms, and
(C) is an organosilicon compound containing SiC-bonded radicals with aliphatic carbon-carbon multiple bonds and Si-bonded hydrogen atoms,
with the proviso that the compositions comprise at least one compound having aliphatic carbon-carbon multiple bonds and at least one compound having Si-bonded hydrogen atoms, and
(ii) at least one
(D) platinum catalyst of the formula (I).

The compounds (A), (B) and (C) used in the compositions of the invention are selected in accordance with the prior art, such that they can be converted to a crosslinked state. For example, compound (A) may have at least two aliphatically unsaturated radicals and (B) at least three Si-bonded hydrogen atoms, or compound (A) may have at least three aliphatically unsaturated radicals and siloxane (B) at least two Si-bonded hydrogen atoms, or, rather than compounds (A) and (B), it is possible to use a siloxane (C) having aliphatically unsaturated radicals and Si-bonded hydrogen atoms, such that crosslinking of the components is possible. Additionally possible are mixtures of (A), (B) and (C) of aliphatically unsaturated radicals and Si-bonded hydrogen atoms.

The quantitative ratios of components (A), (B) and (C) used in accordance with the invention correspond to those known from the prior art. The platinum catalyst (D) is used in such amounts that, based on the Pt(0) content, the amounts of catalyst known from the prior art are likewise present in the composition of the invention.

The compound (A) used in accordance with the invention may comprise silicon-free organic compounds preferably having at least two aliphatically unsaturated groups and organosilicon compounds preferably having at least two aliphatically unsaturated groups, or mixtures thereof Preferably, component (A), if it comprises organosilicon siloxane compounds, does not contain any adjacent siloxy groups with monovalent radicals having aliphatic carbon-carbon multiple bonds R″, i.e. has no R″Si—O—SiR″-moieties.

Examples of silicon-free organic compounds (A) are 1,3,5-trivinylcyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, methylcyclopentadiene, 5-vinyl-2-norbornene, bicyclo[2.2.1]hepta-2,5-diene, 1,3-diisopropenylbenzene, polybutadiene containing vinyl groups, 1,4-divinylcyclohexane, 1,3,5-triallylbenzene, 1,3,5-trivinylbenzene, 1,2,4-trivinylcyclohexane, 1,3,5-triisopropenylbenzene, 1,4-divinylbenzene, 3-methyl-1,5-heptadiene, 3-phenyl-1,5-hexadiene, 3-vinyl-1,5-hexadiene and 4,5-dimethyl-4,5-diethyl-1,7-octadiene, N,N'-methylenebisacrylamide, 1,1,1-tris(hydroxymethyl)propane triacrylate, 1,1,1-tris(hydroxymethyl)propane trimethacrylate, tripropylene glycol diacrylate, diallyl ether, diallyl carbonate, N,N'-diallylurea, polyethylene glycol diacrylate and polyethylene glycol dimethacrylate.

Preferably, the silicone compositions of the invention comprise, as constituent (A), at least one aliphatically unsaturated organosilicon compound, it being possible to use any of the aliphatically unsaturated organosilicon compounds useful in addition-crosslinking compositions.

If (A) is an organosilicon compound having SiC-bonded radicals with aliphatic carbon-carbon multiple bonds, it preferably comprises linear or branched organopolysiloxanes composed of units of the general formula $$R^{11}_{a}R^{12}_{b}SiO_{(4-a-b)/2} \quad (IV),$$

where
$R^{11}$ may be the same or different and is a hydroxyl radical or a monovalent, optionally halogen-substituted, aliphatically saturated hydrocarbyl radical which has 1 to 20 carbon atoms and optionally contains oxygen, nitrogen, sulfur or phosphorus atoms, $R^{12}$ may be the same or different and is a monovalent, optionally halogen-substituted, aliphatically unsaturated hydrocarbyl radical which has 2 to 10 carbon atoms and optionally contains oxygen, nitrogen, sulfur or phosphorus atoms, a is 0, 1, 2 or 3,
b is 0, 1, 2 or 3, preferably an average of 0.0001 to 2, with the proviso that the sum of $a+b \leq 4$, on average $1.5 < (a+b) \leq 3$, and that at least two aliphatically unsaturated $R^{12}$ radicals are present per molecule, where no units of the formula (IV) with b different than 0 are joined to one another in the molecule.

Preferably, the $R^{12}$ radical comprises halogen-substituted hydrocarbyl radicals which have 2 to 10 carbon atoms, optionally contain oxygen, nitrogen, sulfur or phosphorus atoms and have a terminal carbon-carbon double bond.

The organosilicon compounds (A) used in accordance with the invention preferably have a viscosity at 25° C. of 1 to 40,000,000 mPa·s, more preferably 50 to 1,000,000 mPa·s.

The viscosities are determined in accordance with DIN EN ISO 3219: 1994 (Polymers/resins in the liquid state or as emulsions or dispersions) and DIN 53019 (Measurement of viscosities and flow curves by means of rotational viscometers) on an Anton Paar MCR301 air-bearing rheometer with plate/cone systems at 25° C.

Organosilicon compounds (B) may be any hydrogen-functional organosilicon compounds which are useful in addition-crosslinkable compositions.

Organosilicon compounds (B) containing Si—H-bonded hydrogen atoms are preferably linear or branched organopolysiloxanes composed of units of the general formula $$R^{13}_{c}H_{d}SiO_{(4-c-d)/2} \quad (V)$$

where
$R^{13}$ may be the same or different and is as defined for the $R^{11}$ radical,
c is 0, 1, 2 or 3 and
d is 0, 1 or 2,
with the proviso that the sum of $c+d \leq 4$ and the organosilicon compound has at least 2 Si-bonded hydrogen atoms per molecule.

An example of component (B) is $Me_3Si—O—[(Me_2SiO)_{90}(MeHSiO)_{10}]—SiMe_3$.

The organosilicon compounds (B) used in accordance with the invention preferably have a viscosity at 25° C. of 100 to 40,000,000 mPa·s, more preferably 1000 to 500,000 mPa·s.

Preferably, constituents (A), (B) or (C) are present in such an amount in the crosslinkable compositions of the invention that the molar ratio of SiH groups to aliphatically unsaturated groups is 0.1 to 20, more preferably 1.0 to 5.0.

Rather than components (A) and (B), the compositions of the invention may contain organosilicon compounds (C) simultaneously having aliphatic carbon-carbon multiple bonds and Si-bonded hydrogen atoms. It is also possible for the compositions of the invention to contain all three components (A), (B) and (C). If organosilicon compounds (C) are used, they are preferably those composed of units of the general formulae $$R^{11}_{g}SiO_{4-g/2} \quad (VII),$$

$$R^{11}_{h}R^{12}SiO_{3-h/2} \quad (VIII) \text{ and}$$

$$R^{11}_{i}HSiO_{3-i/2} \quad (IX),$$

where $R^{11}$ and $R^{12}$ may be the same or different and are as defined above,
g is 0, 1, 2 or 3,
h is 0, 1 or 2 and
i is 0, 1 or 2, with the proviso that at least 2 $R^{12}$ radicals and at least 2 Si-bonded hydrogen atoms are present per molecule.

Examples of organopolysiloxanes (C) are those composed of $SiO_{4/2}$, $R^{11}_{3}SiO_{1/2}$, $R^{11}_{2}R^{12}SiO_{1/2}$ and $R^{11}_{2}HSiO_{1/2}$ units, called MQ resins, where these resins may additionally contain $R^{11}SiO_{3/2}$ and $R^{11}_{2}SiO_{2/2}$ units, and linear organopolysiloxanes essentially consisting of $R^{11}_{2}R^{12}SiO_{1/2}$, $R^{11}_{2}SiO_{2/2}$ and $R^{11}HSiO_{2/2}$ units with $R^{11}$ and $R^{12}$ as defined above.

The organopolysiloxanes (C) preferably have a viscosity of 0.01 to 500,000 mPa·s, more preferably 0.1 to 100,000 mPa·s, in each case at 25° C.

The components (A), (B) and (C) usable in accordance with the invention are standard commercial products or are preparable by standard chemical methods.

The amount of the platinum complex (D) used is guided by the desired crosslinking rate and economic aspects. Typically, for every 100 parts by weight of crosslinkable composition, preferably $1 \cdot 10^{-3}$ to $5 \cdot 10^{-2}$ parts by weight, more preferably $1 \cdot 10^{-4}$ to $1 \cdot 10^{-2}$ parts by weight, especially $5 \cdot 10^{-4}$ to $5 \cdot 10^{-3}$ parts by weight, of platinum complexes are used, in each case calculated as platinum metal.

As well as the abovementioned components (A), (B), (C) and (D), it is also possible for further components to be present in the compositions of the invention, for example inhibitors and stabilizers (E), fillers (F), and additives (G).

Components (E) serve for controlled adjustment of the processing time, the onset characteristics and the crosslinking rate of the compositions of the invention. These inhibitors and stabilizers are very well known in the field of addition-crosslinking compositions. Examples of commonly used inhibitors are acetylenic alcohols, such as 1-ethynyl-1-cyclohexanol, 2-methyl-3-butyn-2-ol and 3,5-dimethyl-1-hexyn-3-ol, 3-methyl-1-dodecyn-3-ol, polymethylvinylsiloxanes which, by contrast with the organosilicon compounds (A), have adjacent $R^{12}Si$—O—$SiR^{12}$ units with $R^{12}$=—CH=—$CH_2$, and which have inhibiting action, for example 1,3,5,7-tetravinyltetramethyltetracyclosiloxane, divinyltetramethydisiloxane, tetravinyldimethyldisiloxane, trialkyl cyanurates, alkyl maleates, such as diallyl maleates, dimethyl maleate and diethyl maleate, alkyl fumarates, such as diallyl fumarate and diethyl fumarate, organic hyperoxides such as cumene hydroperoxide, tert-butyl hydroperoxide and pinane hydroperoxide, organic peroxides, organic sulfoxides, organic amines, diamines and amides, phosphines and phosphites, nitriles, triazoles, diaziridines and oximes.

Preferably, component (E) comprises acetylenic alcohols and alkyl maleates.

The effect of these inhibitor additions (E) depends on their chemical structure, and so the concentration has to be determined individually. If inhibitors (E) are used, the amounts are preferably 0.00001% by weight to 5% by weight, more preferably 0.00005% to 2% by weight, especially preferably 0.0001% to 1% by weight, based in each case on the total weight of the composition of the invention. Component (E) is added with preference.

Any fillers (F) used in the compositions of the invention may be any desired fillers known to date.

Examples of fillers (F) are non-reinforcing fillers, i.e. fillers having a BET surface area of preferably up to 50 m$^2$/g, such as quartz, diatomaceous earth, calcium silicate, zirconium silicate, talc, kaolin, zeolites, metal oxide powders such as aluminum oxides, titanium oxides, iron oxides or zinc oxides or mixed oxides thereof, barium sulfate, calcium carbonate, gypsum, silicon nitride, silicon carbide, boron nitride, glass and polymer powders, such as polyacrylonitrile powder; reinforcing fillers, i.e. fillers having a BET surface area of more than 50 m$^2$/g, such as precipitated chalks, carbon black, such as furnace black and acetylene black, and mixed silicon-aluminum oxides of high BET surface area; aluminum trihydroxide, hollow spherical fillers, such as ceramic microbeads, for example those available under the Zeeospheres™ trade name from 3M Deutschland GmbH in Neuss, Germany, elastic polymer beads, for example those obtainable under the EXPANCEL® trade name from AKZO NOBEL, Expancel in Sundsvall, Sweden, or glass beads; fibrous fillers, such as asbestos, and polymeric fibers. The fillers mentioned may have been hydrophobized, for example by treatment with organosilanes or -siloxanes or with stearic acid or by etherification of hydroxyl groups to give alkoxy groups.

If the compositions of the invention comprise fillers (F), these are preferably fumed and precipitated silicas having BET surface areas of at least 50 m$^2$/g.

Any fillers (F) used have a moisture content of preferably below 1% by weight, more preferably below 0.5% by weight.

If the compositions of the invention comprise fillers (F), the amounts are preferably 0.1% to 70% by weight, more preferably 1% to 50% by weight, especially 10% to 30% by weight, based in each case on the total weight of the composition of the invention. The compositions of the invention preferably comprise fillers (F).

Examples of any components (G) used are any further additions which have also been used to date for production of addition-crosslinking compositions, such as resinous polyorganosiloxanes other than the siloxanes (A), (B) and (C), fungicides, fragrances, organic rheological additives, corrosion inhibitors, oxidation inhibitors, light stabilizers other than the fillers (F), organic flame retardants and agents for influencing the electrical properties other than the fillers (F), dispersing aids, solvents, adhesion promoters, pigments, dyes, plasticizers other than the siloxanes (A), (B) and (C), organic polymers and heat stabilizers.

The additions (G) are preferably resinous polyorganosiloxanes, solvents, adhesion promoters, pigments and dyes.

If the compositions of the invention comprise additions (G), the amounts are preferably 0% to 30% by weight, more preferably 1% to 20% by weight, especially 1% to 5% by weight, based in each case on the total weight of the composition of the invention. The compositions of the invention preferably comprise additions (G).

The compositions of the invention preferably do not comprise any further constituents apart from components (A) to (G).

Components (A), (B) and (C), and (E), (F) and (G), are preferably transparent below 400 nm, more preferably from 200 to 400 nm, such that light-induced crosslinking of the compositions can be effected by activation of the catalyst (D).

The components used in accordance with the invention may each be one kind of such a component or a mixture of at least two kinds of any particular component.

The compositions of the invention may, if required, be dissolved, dispersed, suspended or emulsified in liquids.

The compositions of the invention may—especially according to the viscosity of the constituents and the filler content—be of low viscosity and pourable, have a pasty consistency, be pulverulent or else be malleable compositions of high viscosity, as can be the case, as is known, for the compositions frequently referred to among experts as RTV-1, RTV-2, LSR and HTV. More particularly, the compositions of the invention, if they are highly viscous, can be prepared in the form of pellets. In this case, the individual pellet particles may comprise all the components, or the components used in accordance with the invention are incorporated separately into different pellet particles. With regard to the elastomeric properties of the crosslinked silicone compositions of the invention, the whole spectrum is likewise covered, starting from extremely soft silicone gels through rubberlike materials up to and including highly crosslinked silicones having glass-like characteristics.

The compositions of the invention can be produced in any desired manner known per se, for instance by methods and mixing processes that are customary for production of addition-crosslinking compositions.

The present invention further provides a process for producing the compositions of the invention by mixing the individual components in any sequence.

This mixing can be effected at room temperature and the pressure of the surrounding atmosphere, i.e. about 900 to 1100 hPa. If desired, this mixing can also be effected at higher temperatures, for example at temperatures in the range from 30 to 130° C. In addition, it is possible to mix temporarily or constantly under reduced pressure, for example at absolute pressure 30 to 500 hPa, in order to remove volatile compounds and/or air.

The mixing of the invention is preferably effected with exclusion of moisture and light with a wavelength of less than 500 nm.

The process of the invention can be conducted continuously or batchwise.

In a preferred embodiment of the process of the invention, platinum catalyst (D) is mixed homogeneously with a mixture of (A), (B), and optionally (E), (F) and (G). The platinum catalyst (D) used in accordance with the invention can be incorporated as a substance or as a solution—dissolved in a suitable solvent—or as a masterbatch—mixed homogeneously with a small amount of (A) or (A) with (E).

The compositions of the invention may be either one-component silicone compositions or two-component silicone compositions.

In the latter case, the two components of the compositions of the invention may comprise all the constituents in any quantitative ratios. Preferably, one component comprises the platinum catalyst (D) and no Si—H-containing component (B) or (C).

The compositions of the invention that are crosslinkable by addition of Si-bonded hydrogen onto an aliphatic multiple bond can be crosslinked under the same conditions as the compositions crosslinkable by hydrosilylation reaction that are known to date.

Preferably, the crosslinking is conducted at a pressure of 30 to 250000 hPa, especially at the pressure of the surrounding atmosphere, i.e. about 900 to 1100 hPa, and at pressures as customary in an injection molding machine, i.e. about 200000 hPa.

Preferably, the crosslinking is conducted at a temperature of 0 to 100° C., especially at 10 to 50° C.

Preferably, the crosslinking is initiated by irradiation, particularly by means of ultraviolet radiation (UV) at 230 to 400 nm, especially 250 to 350 nm. Depending on the formulation, the catalyst and the intensity of the UV radiation, the necessary irradiation time may preferably be less than 1 minute, more preferably less than 1 second. It is possible to use any radiation source having radiation components below about 400 nm. Wavelengths less than 230 nm should preferably not be used. Conventional low-, medium- and high-pressure mercury lamps are suitable. Radiation sources such as fluorescent lamps and "blacklight lamps" are likewise suitable.

The necessary radiation density depends on many factors and corresponds to that of crosslinkable systems comprising, for example, Cp'PtMe$_3$, which correspond to the prior art. For instance, the necessary radiation dose for the commercially available SEMICOSIL® 912/ELASTOSIL® CAT UV (10:1) composition, in the wavelength range of 250 to 350 nm (produced, for example, by means of an Fe-doped mercury lamp), is 1.5 J/cm$^2$ for 2 minutes, corresponding to a radiation density of 180 mW/cm$^2$.

The present invention further provides shaped bodies produced by crosslinking the compositions of the invention.

The compositions of the invention and the crosslinking products produced therefrom in accordance with the invention can be used for any purposes for which organopolysiloxane compositions crosslinkable to elastomers or elastomers have been used to date. This includes, for example, the silicone coating or impregnation of any desired substrates, the production of moldings, for example in an injection molding method, vacuum extrusion method, extrusion method, casting and compression molding, and impressions, use as sealing, embedding and potting compounds, etc.

The crosslinkable compositions of the invention have the advantage that they can be produced in a simple process using readily obtainable starting materials, and hence in an economically viable manner.

The crosslinkable compositions of the invention have the further advantage that they have good storage stability in the form of a one-component formulation at 25° C. and ambient pressure, and only crosslink on irradiation by visible or ultraviolet radiation. The crosslinking time is dependent on the duration and intensity of the radiation.

The compositions of the invention also have the advantage that they give rise, in the case of a two-component formulation, after mixing of the two components, to a crosslinkable silicone composition which remains processible over a long period at 25° C. and ambient pressure, i.e. exhibit an extremely long pot life, and only crosslink on irradiation.

In the production of the crosslinkable compositions of the invention, it is highly advantageous that the platinum catalyst (D) can be dosed efficiently and incorporated easily.

The compositions of the invention additionally have the advantage that the crosslinked silicone rubbers obtained therefrom have excellent transparency.

The compositions of the invention also have the advantage that the hydrosilylation reaction does not slow with reaction time and does not automatically stop after the irradiation has ended. Regions that have not been directly exposed also cure, which is advantageous particularly in the case of detailed impressions or in the potting of electronic components. An increase in temperature cannot initiate but can accelerate the crosslinking.

The use of the inventive platinum complexes of the formula (I) in crosslinkable compositions has the advantage over systems used to date that they bring about better dark stability, i.e. long storage stability, of crosslinkable preparations.

In the context of the present invention, the term "organopolysiloxanes" encompasses polymeric, oligomeric and dimeric siloxanes.

In the examples described hereinafter, all parts and percentage figures, unless stated otherwise, are based on weight. Unless stated otherwise, the examples which follow are conducted at a pressure of the surrounding atmosphere, i.e. at about 1000 hPa, and at room temperature, i.e. at about 20° C., or at a temperature which is established on combination of the reactants at room temperature without additional heating or cooling.

The viscosities are determined in accordance with DIN EN ISO 3219: 1994 (Polymers/resins in the liquid state or as emulsions or dispersions) and DIN 53019 (Measurement of viscosities and flow curves by means of rotational viscometers) on an Anton Paar MCR301 air-bearing rotational rheometer with plate/cone systems at 25° C.

The following abbreviations are used:

Me: methyl radical

Gel Time

The gel time is determined at 120° C. with a Bachofer GELNORM gel timer, with the uncrosslinked composition in a 160×15.75 mm test tube according to DIN 16 945-1. The gel time is considered to be the period of time between commencement of testing and the juncture at which the reaction mixture moves from the liquid to the gelated state. The determination is conducted with exclusion of light with wavelengths in the range of <500 nm.

Penetration

The penetration is determined at 25° C. on a Petrotest Instruments PNR10 penetrometer according to DIN ISO 2137 with a quarter-cone of weight 9.38 g after a penetration time of 5 seconds. The sample to be analyzed was exposed beforehand at 10 seconds at 1000 W in a UV Cube (from Hoehnle; about 70 mW/cm$^2$) by means of an iron radiation source of wavelength 230-400 nm and heat-treated at 150° C. for 30 min. The penetration depth is reported in $\frac{1}{10}$ mm.

Preparation of Cyclopentadienyl-Functionalized Silane 1:

To 17.6 g (200 mmol) of sodium cyclopentadienide in 100 mL of absolute tetrahydrofuran are added dropwise, at 0° C. within one hour, 28.6 g (0.21 mmol) of allyldimethylchlorosilane. After the solvent has been drawn off, the mixture is extracted with water/diethyl ether (1/1 v/v) and the organic phase is fractionally distilled in order to obtain, in 55% yield, 18.1 g of allyldimethylsilylcyclopentadiene.

Preparation of Cyclopentadienyl-Functionalized Silane 2:

To a suspension of 4.8 g (200 mmol) of sodium hydride in 250 mL of absolute tetrahydrofuran are added dropwise, at room temperature within one hour, 32.8 g (200 mmol) of allyldimethylsilylcyclopentadiene. Subsequently, within 30 minutes, 36.4 g (200 mmol) of (3-chloropropyl)dimethoxymethylsilane are added dropwise. In the course of this, the solution warms up. After the solvent has been drawn off, fractional distillation is effected in an oil-pump vacuum, in order to obtain, in 81% yield, 50.2 g of (3-dimethoxymethylsilylpropyl) (allyldimethylsilyl)cyclopentadiene.

Preparation of Cyclopentadienyl-Functionalized Silane 3:

To 16.4 g (100 mmol) of allyldimethylsilylcyclopentadiene in 250 mL of absolute diethyl ether are added dropwise, at room temperature within one hour, 62.5 mL of 1.6 mol/L butyllithium in diethyl ether (100 mmol). Subsequently, within 30 minutes, 13.4 g (100 mmol) of allyldimethylchlorosilane are added dropwise. In the course of this, the solution warms up. After the solvent has been drawn off, fractional distillation is effected in an oil-pump vacuum, in order to obtain, in 60% yield, 15.7 g of bis(allyldimethylsilyl)cyclopentadiene.

Example 1

Preparation of Platinum Complex 1

To a solution of 4.92 g (30 mmol) of silane 1 in 50 mL of absolute tetrahydrofuran are added 14.1 g (33 mmol) of 15% butyllithium solution in hexane. To this are added 7.34 g of trimethylplatinum(IV) iodide (20 mmol), and the mixture is stirred at room temperature for two hours. After the solvent has been drawn off, the platinum complex is distilled at a pressure of 10$^{-4}$ hPa for purification. 6.8 g of pure trimethyl [(allyldimethylsilyl)cyclopentadienyl]platinum(IV) are obtained in 84% yield.

Example 2

Preparation of Platinum Complex 2

To a solution of 9.3 g (30 mmol) of silane 2 in 50 mL of absolute tetrahydrofuran is added 0.72 g (30 mmol) of sodium hydride. To this are added 9.15 g of trimethylplatinum(IV) iodide (25 mmol), and the mixture is stirred at room temperature for two hours. After the solvent has been drawn off, the platinum complex is distilled at a pressure of 10$^{-4}$ hPa for purification. 11.0 g of pure trimethyl[(3-dimethoxymethylsilylpropyl) (allyldimethylsilyl)cyclopentadienyl]platinum(IV) is obtained in 80% yield.

Example 3

Preparation of Platinum Complex 3

To a solution of 7.9 g (30 mmol) of silane 3 in 50 mL of absolute tetrahydrofuran are added 14.1 g (33 mmol) of 15% butyllithium solution. To this are added 7.34 g of trimethylplatinum(IV) iodide (20 mmol) and the mixture is stirred at room temperature for two hours. After the solvent has been drawn off, the platinum complex is distilled at a pressure of 10$^{-4}$ hPa for purification. 7.5 g of pure trimethyl [bis(allyldimethylsilyl)cyclopentadienyl]platinum(IV) is obtained in 75% yield.

Comparative Example 1

Platinum Complex 4

The commercially available platinum complex trimethyl (methylcyclopentadienyl)platinum(IV) serves as a comparative example, and is used directly as catalyst. It does not bear any further functional groups.

Example 4

Cohydrolysis of Platinum Complex 2 from Example 2

2.5 g of platinum complex 2, 98 g of α,ω-silanol-terminated polydimethylsiloxane [CAS 70131-67-8] with a viscosity of 1000 mPa·s and 0.025 g of aluminum tris(2,4-pentanedionate) are mixed at 25° C. and stirred at room temperature for a period of 24 hours. About 100 g of a siloxane-bonded complex are obtained with elimination of methanol; to remove the methanol, volatiles are removed at 25° C. and 1 mbar for 30 min.

Example 5

Gel Time at 120° C.:

The gel time is determined with a mixture of 2 g of Me$_3$Si—O—[(Me$_2$SiO)$_{90}$(MeHSiO)$_{10}$]—SiMe$_3$ and 18 g of a 300 ppm solution of platinum complex 1 from example 1 in ViMe$_2$Si—O—[(Me$_2$SiO)$_n$]—SiMe$_2$Vi (viscosity 1000 mPa·s at 25° C.) at 120° C. The mixture gelates after 9 h 36 min.

Gel time of platinum complex 2 from example 2:

Gel time of platinum complex 3 from example 3:

The gel time with platinum complex 4 from comparative example 1 is 15 min.

It is found that the dark stability of the complexes of the invention is distinctly greater.

Gelation Test 0.042 g of a 10% chloroform solution of platinum complex 1 from example 1 is mixed into 20 g of ViMe$_2$Si—O—[(Me$_2$SiO)$_n$]—SiMe$_2$Vi (viscosity 1000 mPa·s at 25° C.). 5 g of this mixture are mixed with 50 g of a formulation crosslinkable by hydrosilylation, containing linear and branched vinyl-functional siloxanes and Si—H-functional siloxanes (commercially available under the Semicosil® 912 name from Wacker Chemie AG, Munich, Germany); the Pt concentration is 9 ppm.

The mixtures comprising platinum complexes 2, 3 and 4 are prepared analogously.

The gel time of the mixture with use of platinum complex 1 from example 1 at 120° C. was 8 h 11 min; after storage at 25° C. for 68 days it was 9 h 58 min.

Gel time of platinum complex 2 from example 2:

Gel time of platinum complex 3 from example 3:

By comparison, the gel time with use of platinum complex 4 from comparative example 1 is: 1 h 30 min.

It is found that the dark stability of the mixtures comprising complexes of the invention is much greater. Moreover, this stability still exists even after prolonged storage, such that there is also longer storage stability of one-component compositions overall.

After storage at 25° C. for 110 days, the mixture comprising platinum complex 1 from example 1 has gelated.

By comparison, the mixture comprising platinum complex 4 from comparative example 1 gelates after 15 days.

Thus, one-component compositions have long storage stability.

The penetration of the elastomer which was obtained by the curing of the mixture comprising platinum complex 1 from example 4 was 68 1/10 mm; after storage at 25° C. for 68 days, it was still 68 1/10 mm.

Penetration of platinum complex 2 from example 2:

Penetration of platinum complex 3 from example 3:

It is found that mixtures comprising the catalysts of the invention, even after storage, do not exhibit any change in the properties of the shaped bodies produced therefrom.

The invention claimed is:

1. A platinum complex of the formula $$R^3_3Pt\{CpR^4_{5-r-t}[(CR_2)_nSiR^1_oR^2_p]_r[SiR^7_sR^8_{3-s}]_t\} \quad (I)$$

where
Cp is a cyclopentadienyl radical,
n is an integer from 1 to 8,
o is 0, 1, 2 or 3,
p is 0, 1, 2 or 3, with the proviso that o+p=3,
r is 1, 2, 3, 4 or 5,
t is 0, 1, 2, 3 or 4, with the proviso that r+t≤5,
s is 0, 1 or 2,
R each is the same or different and is hydrogen or a monovalent unsubstituted or substituted hydrocarbyl radical,
$R^1$ each is the same or different and is a monovalent unsubstituted or substituted hydrocarbyl radical which is optionally interrupted by heteroatoms,
$R^2$ each is the same or different and is a hydrolyzable group or an oxygen-bonded siloxy radical,
$R^7$ each is the same or different and is a monovalent, unsubstituted or substituted, aliphatically saturated hydrocarbyl radical which may be interrupted by heteroatoms, or an oxygen-bonded siloxy radical,
$R^8$ each is the same or different and is an aliphatically unsaturated, optionally substituted radical,
$R^3$ each is the same or different and is a monovalent, unsubstituted or substituted, aliphatically saturated hydrocarbyl radical,
$R^4$ each is the same or different and is a hydrogen atom, SiC-bonded silyl radical or an unsubstituted or substituted hydrocarbyl radical which may be interrupted by heteroatoms.

2. The platinum complex of claim 1, wherein the $R^2$ radical, each individually, comprises an alkoxy, carboxyl or siloxy radical.

3. The platinum complex of claim 1, wherein the $R^8$ radical comprises radicals of the formula $$-CR^{10}_2-CR^{10}=CR^{10}_2$$

where $R^{10}$ each is the same or different and is as defined for the R radical.

4. The platinum complex of claim 2, wherein the $R^8$ radical comprises radicals of the formula $$-CR^{10}_2-CR^{10}=CR^{10}_2$$

where $R^{10}$ each is the same or different and is as defined for the R radical.

5. The platinum complex of claim 3, wherein the $R^{10}$ radical is a methyl radical or hydrogen.

6. The platinum complex of claim 3, wherein the $R^8$ radical comprises allyl radicals of the formula $$-CH_2-CH=CH_2.$$

7. The platinum complex of claim 2, wherein the $R^8$ radical comprises allyl radicals of the formula $$-CH_2-CH=CH_2.$$

8. A process for preparing a platinum complex of the formula (I) of claim 1, comprising reacting one or more cyclopentadienide salts with at least one triorganoplatinum (IV) halide.

9. An addition-crosslinking composition, comprising at least one platinum complex of claim 1.

10. The composition of claim 9, comprising
(i) at least one compound selected from the group consisting of compounds (A), (B) and (C), where
(A) is an organic compound and/or an organosilicon compound containing at least two radicals having aliphatic carbon-carbon multiple bonds,
(B) is an organosilicon compound containing at least two Si-bonded hydrogen atoms, and
(C) is an organosilicon compound containing SiC-bonded radicals with aliphatic carbon-carbon multiple bonds and Si-bonded hydrogen atoms,
with the proviso that the compositions comprise at least one compound having aliphatic carbon-carbon multiple bonds and at least one compound having Si-bonded hydrogen atoms, and
(ii) at least one
(D) platinum catalyst of the formula (I) of claim 1.

11. A process for producing a composition of claim 10, comprising mixing the individual components in any sequence.

12. A shaped body produced by crosslinking a composition of claim 9.

13. A shaped body produced by crosslinking a composition of claim 10.

* * * * *